United States Patent [19]

Labrie et al.

[11] Patent Number: 4,775,660

[45] Date of Patent: Oct. 4, 1988

[54] TREATMENT OF BREAST CANCER BY COMBINATION THERAPY

[76] Inventors: Fernand Labrie, 2735 boul Liegeois, St. Foy, Quebec, G1W 1Z9; Alain Bélanger, 4031 Bois Verdun, Cap-Rouge PQ, Quebec, G0A 1K0; André Dupont, 3371 Chemin St. Louis, St. Foy, Quebec, G1W 1S1, all of Canada

[21] Appl. No.: 636,883

[22] Filed: Aug. 2, 1984

[51] Int. Cl.$^4$ .............................................. A61K 37/43
[52] U.S. Cl. ...................................... 514/15; 514/800
[58] Field of Search .................................. 514/15, 800

[56] References Cited

U.S. PATENT DOCUMENTS

| | | | |
|---|---|---|---|
| 4,024,248 | 5/1977 | König et al. | 424/177 |
| 4,071,622 | 1/1978 | Johnson et al. | 424/177 |
| 4,094,994 | 6/1978 | Schönenberger et al. | 424/341 |
| 4,097,578 | 6/1978 | Perronnet et al. | 424/273 R |
| 4,118,483 | 10/1978 | König et al. | 424/177 |
| 4,329,364 | 5/1982 | Neri et al. | 424/324 |
| 4,472,382 | 9/1984 | Labrie et al. | 424/177 |
| 4,666,885 | 5/1987 | Labrie | 514/15 |

FOREIGN PATENT DOCUMENTS

| | | |
|---|---|---|
| 637389 | 3/1964 | Belgium . |
| 78158 | 5/1983 | European Pat. Off. . |

OTHER PUBLICATIONS

Miller et al., Nature, 313 (1985), pp. 231-233.
Cancer Treatment Reports, vol. 68 (No. 1), pp. 281-289 (1984), A. V. Schally et al.
Proc. Natl. Acad. Sci. USA., vol. 80, pp. 1459-1462 (1983), T. W. Redding and A. V. Schally.
"LH-RH Analogs in the Treatment of Human Breast Cancer", H. A. Harvey et al. in *LHRH and Its Analogs—A New Class of Contraceptive and Therapeutic Agents*, (R. H. Vickery et al., eds), MTP Press, Lancaster, U. K. (1984), pp. 329-335.
Lancet, 1, 1213-1216 (1982), J. G. M. Klijn et al. (The Lancet, May 29, 1982).
Cancer, vol. 50, 1708-1712 (1982), A. V. Buzdar et al.
Lancet, 1204-1207 (1973), H. Flax et al., (The Lancet; Jun. 2, 1973).
The Prostate, vol. 4, 579-594 (1983), F. Labrie et al.
J. Steroid Biochem., vol. 19, 99-1007 (1983), F. Labrie et al.
Cancer Treatment Review, vol. 5, 131-141 (1978), H. Movridsen et al.
J. Steroid Biochem., vol. 20 (No. 6B), 1381 (1984), J. G. M. Klijn et al.
J. Med. Chem., vol. 21, 1018-1024 (1978), A. S. Dutta et al.
Biochem. Biophy. Res. Commun., vol. 100, pp. 915-920 (1981), J. Erchegyi et al.
Endocrinology, vol. 110, pp. 1445-1447 (1982); D. H. Coy et al.
J. Steroid. Biochem., vol. 20 (No. 6B), 1366 (1984); J. J. Nestor et al.
J. Steroid. Biochem., vol. 20 (No. 6B), 1365 (1984); J. Rivier et al.
J. Steroid. Biochem., vol. 20 (No. 6B), p. 1369 (1984); A. Corbin et al.
"Solid Phase Peptide Synthesis", Stewart et al., Freeman et al., San Francisco, CA (1969), pp. 1-26.
J. Med. Chem., vol. 19, pp. 423-425 (1976), D. H. Coy et al.

*Primary Examiner*—Delbert R. Phillips
*Attorney, Agent, or Firm*—Ostrolenk, Faber, Gerb & Soffen

[57] ABSTRACT

A method of treatment of breast cancer in susceptible animals whose ovarian hormonal secretions were previously blocked by surgical or chemical means, e.g., by use of an LH-RH agonist, e.g., [D-Trp$^6$, des-Gly-NH$_2^{10}$]LH-RH ethylamide with a combination therapy comprising administering an antiandrogen, e.g., flutamide and an antiestrogen, e.g., Tamoxifen, pharmaceutical compositions useful for such treatment and two and three component pharmaceutical kits containing such compositions are disclosed.

40 Claims, No Drawings

TREATMENT OF BREAST CANCER BY COMBINATION THERAPY

BACKGROUND OF THE INVENTION

This invention relates to a method of treatment of breast cancer in susceptible warm-blooded animals using a combination therapy comprising administering an antiandrogen and an antiestrogen to such animals after the hormone output of their ovaries has been blocked. The invention also includes pharmaceutical compositions useful for such treatment and pharmaceutical kits containing such compositions. In its most preferred aspect, this invention relates to treatment of breast cancer in warm-blooded animals by parenterally administering an LH-RH agonist, orally administering an antiandrogen and orally administering an antiestrogen.

While various investigators have been studying hormone-dependent breast and prostrate cancer, none have proposed the combination therapy of this invention.

A. V. Schally et al., Cancer Treatment Reports, 68, (No. 1) 281–289 (1984), summarize the results of animal and clinical studies on growth inhibition of hormone-dependent mammary and prostate tumors by use of analogues of luteinizing hormone-releasing hormones, the so-called LH-RH agonists and suggest that LH-RH analogs and/or antagonists may have potential for treating breast cancer.

T. W. Redding and A. V. Schally, Pro. Natl. Acad. Sci. USA, 80, 1459–1462 (1983), disclose reduction of estrogen-dependent mammary tumors in rats and mice by use of an LH-RH agonist, [D-Trp$^6$]LH-RH or of two specific antagonists.

In U.S. Pat. No. 4,071,622, it is disclosed that use of certain LH-RH agonists causes regression of DMBA-induced mammary carcinoma in rats.

Some clinical improvement in premenopausal women with breast cancer by use of the two LH-RH agonists, Buserelin and Leuprolide, is also reported by H. A. Harvey et al. "LH-RH analogs in the treatment of human breast cancer", *LH-RH and its Analogs - A New Class of Contraceptive and Therapeutic Agents* (B. H. Vickery and J. J. Nestor, Jr., and E. S. E. Hafez, eds) Lancester, MTP Press, (1984) and by J. G. M. Klijn et al. "Treatment with luteinizing hormone releasing hormone analogue (Buserelin) in premenopausal patients with metastatic breast cancer", Lancet, 1, 1213–1216 (1982).

Treatment of advanced breast cancer with aminoglutethimide after therapy with the antiestrogen, Tamoxifen is disclosed by A. V. Buzdar et al., Cancer, 50, 1708–1712 (1982).

H. Flax et al., Lancet, 1204–1207, (1973), suggest some women's breast cancers are androgen-dependent.

F. Labrie et al., The Prostrate, 4, 579–594 (1983), disclose that use of a combination therapy of an LH-RH agonist (Buserelin) and an antiandrogen (Anandron) to treat advanced prostate cancer in previously untreated patients effects complete elimination of androgens of both testicular and adrenal origin.

F. Labrie et al., J. Steroid Biochem., 19, 99–1007 (1983), disclose the treatment of prostate cancer by the combined administration of an LH-RH agonist and an antiandrogen. Labrie et al. disclose animal and clinical data in support of the proposition that the combined LH-RH/antiandrogen treatment completely neutralizes the stimulatory influence of all androgens on the development and growth of androgen-dependent prostatic cancer.

In U.S. Pat. No. 4,094,994, it is disclosed that the use of antiestrogens such as meso-3,4-bis(3'-hydroxyphenyl)hexane inhibits MCF7 human breast tumor cells. In fact, the inhibitory activity of the anti-estrogen was antagonized by estradiol.

H. Mouridsen et al,. Cancer Treatment Review 5, 131–141, (1978), disclose that Tamoxifen, an antiestrogen is effective in remission of advanced breast cancer in about 30% of the women patients treated.

J. G. M. Klijn et al., (J. Steroid Biochem, Vol. 20 (No. 6B), 1381 (1984), the combined use of the antiestrogen, Tamoxifen, and the LH-RH agonist, Buserelin, for treatment of breast cancer is known, but objective remission of such cancers remains low (35%).

BRIEF DESCRIPTION OF THE INVENTION

In its broadest aspect, the invention provides a method of treating breast cancer in a warm-blooded animal in need of such treatment which comprises blocking the ovarian hormonal secretions of said animal by surgical or chemical means and administering to said animal therapeutically effective amounts of an antiandrogen and an antiestrogen, or pharmaceutical compositions thereof. In one aspect, the invention provides a method of treating breast cancer in a warm-blooded animal whose ovaries were previously blocked by surgical or chemical means from secreting estrogen, which comprises administering to an animal in need of such treatment an antiandrogen and an antiestrogen, or pharmaceutical compositions thereof, in amounts sufficient to treat breast cancer. By completely blocking sex-steroids (androgens and estrogens) production and/or action, the present invention provides a method of inhibiting the growth of hormone-sensitive breast tumors in warm-blooded animals having such tumors.

In female mammals, the ovaries may be surgically removed (oophorectomy) but preferably the secretion of estrogen from the ovaries are blocked chemically by administering to warm-blooded animals, i.e., mammals, an effective amount of an LH-RH agonist or antagonist. Thus in a preferred aspect, the present invention provides a method of treating breast cancer in a warm-blooded animal, which comprising administering to an animal in need of such treatment an LH-RH agonist or antagonist, an antiandrogen and an antiestrogen, or pharmaceutical compositions thereof, in amounts sufficient to treat breast cancer.

In its preferred aspect, the LH-RH agonist is administered parenterally (subcutaneously or intramuscularly) and the antiandrogen and the antiestrogen are each administered orally. The invention also provides kits or single packages combining the two and three separate preferred pharmaceutical compositions; the two component kit provides the antiandrogen oral pharmaceutical composition and the antiestrogen oral composition and the three component kit provides the LH-RH agonist parenteral pharmaceutical composition, the antiandrogen oral pharmaceutical composition and the antiestrogen oral pharmaceutical composition.

Thus, this invention provides a novel method for effective treatment of breast cancer. In addition, the amounts of antiestrogen administered in this combined therapy are lower than normally used in the prior art, e.g., J. G. M. Klijn et al., J. Steroid Biochem. 20 (No. 6B) 1381 (1984), to treat breast cancer, and thus, the harmful effects of relatively large doses of antiestrogen are minimized.

DETAILED DESCRIPTION OF THE INVENTION

In one preferred aspect, the present invention provides an effective method of treating breast cancer in warm-blooded animals in need of such treatment by administering an LH-RH agonist, an antiandrogen and an antiestrogen, or pharmaceutical composition thereof in amounts sufficient to inhibit breast tumor growth. These active compounds can be administered together or in any order as discussed hereinafter. To assist in determining the effect of the treatment, blood plasma concentrations of the adrenal androgens and estrogens and tumor size are measured. Lowered concentrations and reduction in tumor size are indicative of successful treatment, e.g. inhibition of tumor growth. The concentrations of adrenal androgens and estrogens such as dehydroepiandrosterone (DHEA), DHEA-Sulfate (DHEAS), androst-5-ene-3$\beta$,17$\beta$-diol ($\Delta^5$-diol) and, the ovarian estrogen, 17$\beta$-estradiol (E2) are measured by standard methods well known to those skilled in the art, see for example F. Labrie et al., The Prostate, 4, 579–594 (1983).

The change in tumor size is measured by standard physical methods well known to those skilled in the art, e.g., bone scan, chest X-ray, skeletal survey, ultrasonography of the liver and liver scan (if needed), CAT-scan and physical examination.

While a LH-RH agonist or a LH-RH antagonist may be used in one preferred aspect of the present invention, the use of a LH-RH agonist is more preferred.

By the term "LH-RH agonist" is meant synthetic analogues of the natural luteinizing hormone-releasing hormone (LH-RH), a decapeptide of the structure:
L-pyroglutamyl-L-histidyl-L-tryptophyl-L-seryl-L-tyrosyl-glycyl-L-leucyl-L-arginyl-L-prolylglycine.

Typical suitable LH-RH agonists include nonapeptides and decapeptides represented by the formula:
L-pyroglutamyl-L-histidyl-L-tryptophyl-L-seryl-L-tyrosyl-X-Y-L-arginyl-L-prolyl-Z
wherein X is D-tryptophyl, D-leucyl, D-alanyl, 3-(2-naphthyl)-D-alanyl, O-tert-butyl-D-seryl, D-tyrosyl, D-lysyl, D-phenylalanyl or N-methyl-D-alanyl and Y is L-leucyl, D-leucyl or D-alanyl and wherein Z is glycyl-NHR$_1$ or NHR$_1$ wherein R$_1$ is H, lower alkyl or lower haloalkyl. Lower alkyl includes straight or branched chain alkyls having 1 to 6 carbon atoms, e.g., methyl, ethyl, propyl, pentyl or hexyls, iso-butyl, neopentyl and the like. Lower haloalkyl includes straight and branched chain alkyls of 1 to 6 carbon atoms having a halogen substituent, e.g., —CF$_3$,—CH$_2$CF$_3$, —CF$_2$CH$_3$. Halogen means F, Cl, Br, with F being preferred.

Preferred nonapeptides wherein Y is L-leucyl and X is an optically active D-form of selected amino acids and Z is NHC$_2$H$_5$ are [D-Trp$^6$, des-gly-NH$_2^{10}$]-LH-RH ethylamide (X=D-Trp$^6$); [D-Ser-(t-BuO)$^6$, des-gly-NH$_2^{10}$]-LH-RH ethylamide [X=D-Ser(t-BuO$^6$)]; [D-Leu$^6$, des-gly-NH$_2^{10}$]-LH-RH ethylamide (X=D-Leu$^6$) and [D-Ala$^6$, des-gly-NH$_2^{10}$]-LH-RH ethylamide (X=D-Ala$^6$).

Preferred decapeptides include [D-Trp$^6$]-LH-RH wherein X=D-Trp, Y=L-leucyl, Z=glycyl-NH$_2$, [D-Phe$^6$]-LH-RH wherein X=D-phenylalanyl, Y=L-leucyl and Z=glycyl-HN$_2$).

Other LH-RH agonists useful within the scope of this invention are the $\alpha$-aza analogues of the natural LH-RH, especially, [D-Phe$^6$,Azgly$^{10}$]-LH-RH, [D-Tyr(Me)$^6$, Azgly$^{10}$]-LH-RH, and [D-Ser-(t-BuO)$^6$,Azgly$^{10}$]-LH-RH disclosed by A. S. Dutta et al. in J. Med. Chem., 21, 1018 (1978) as well as those disclosed in U.S. Pat. Nos. 4,024,248 and 4,118,483.

Typical suitable LH-RH antagonists include [N-Ac-D-p-Cl-Phe$^{1,2}$, D-Phe$^3$, D-Arg$^6$, D-Ala$^{10}$]-LH-RH disclosed by J. Ercheggi et al., Biochem. Biophys. Res. Commun. 100, 915–920, (1981); [N-Ac-D-p-Cl-Phe$^{1,2}$, D-Trp$^3$, D-Arg$^6$, D-Ala$^{10}$]LH-RH disclosed by D. H. Coy et al., Endocrinology, 110: 1445–1447, (1982); [N-Ac-D-(3-(2-naphthyl)-Ala)$^1$, D-p-Cl-Phe$^2$, D-Trp$^3$, D-hArg(Et$_2$)$^6$, D-Ala$^{10}$]-LH-RH and [N-Ac-Pro$^1$, D-p-F-Phe$^2$, D-(3-(2-naphthyl)Ala$^{3,6}$]-LH-RH disclosed by J. J. Nestor et al. J. Steroid Biochem., 20 (No. 6B), 1366 (1984); analogs of the highly constrained cyclic antagonist, cycle [$\Delta^3$ Pro$^1$, D-p-Cl-Phe$^2$, D-Trp$^{3,6}$, N-Me-Leu$^7$, $\beta$-Ala$^{10}$]-LH-RH disclosed by J. Rivier, J. Steroid Biochem., 20, (No. 6B), 1365 (1984), and [N-Ac-D-(3-(2-naphthyl)-Ala$^1$, D-p-F-Phe$^2$, D-Trp$^3$, D-Arg$^6$]-LH-RH disclosed by A. Corbin et al., J. Steroid Biochem. 20 (No. 6B) 1369 (1984).

The LH-RH agonists and antagonists useful in this invention may conveniently be prepared by the method described by Stewart et al. in "Solid Phase Peptide Synthesis" (published in 1969 by Freeman & Co., San Francisco, page 1).

The nona- and decapeptides used in this invention are conveniently assembled on a solid resin support, such as 1% cross-linked Pro-Merrifield resin by use of an automatic peptide synthesizer. Typically, side-chain protecting groups, well known to those in the peptide arts, are used during the dicyclohexylcarbodiimidecataylzed coupling of a tert-butyloxycarbonylamino acid to the growing peptide attached to a benzhydrylamine resin. The tert-butyloxycarbonyl protecting groups are removed at each stage with trifluoroacetic acid. The nona- or decapeptide is cleaved from the resin and deprotected by use of HF. The crude peptide is purified by the usual techniques, e.g., gel filtration and partition chromatography and optionally lyophilization. See also D. H. Coy et al., J. Med. Chem. 19, pages 423–425, (1976).

Typical suitable antiandrogens include nonsteroidal antiandrogens such as the imidazolidines, especially 1-(3'-trifluoromethyl-4'-nitrophenyl)-4,4-dimethyl-imidazoline-2,5-dione (also called Anandron) described in U.S. Pat. No. 4,097,578, or 4'-nitro-3'-trifluoromethylisobutyranilide (also called flutamide) described in U.S. Pat. No. 4,329,364. Flutamide is the preferred antiandrogen.

Typically suitable steroidal antiandrogens include 6-chloro-1,2-dihydro-17-(acetyloxy)-3'H-cyclopropa[1,2]pregna-1,4,6-triene-3,20-dione, available under the tradename of Androcur from Schering A. G., W. Berlin, 17-(acetyloxy)-6-methyl-pregna-4,6-diene-3,20-diene, also called megestrol acetate and available from Mead Johnson & Co., Evansille, Ind. under the tradename of Megace.

Typical suitable antiestrogens include those steroidal and non-steroidal antiestrogens such as (1RS,2RS)-4,4'-diacetoxy-5,5'-difluoro-(1-ethyl-2-methylene)di-m-phenylenediacetate, which is available from Biorex under the tradename of Acefluranol, 6$\alpha$-chloro-16$\alpha$-methyl-pregn-4-ene-3,20-dione which is available from Eli Lilly & Co., Indianapolis, Ind. under the tradename of Clometherone, 6-chloro-17-hydroxypregna-1,4,6-triene-3,20-dione which is available as the acetate salt from Syntex Labs, Palo Alto, Cal. as Delmadione Acetate, 17-hydroxy-6-methyl-19-norpregna-4,6-diene-3,20-dione which is available from Theramex under the name of Lutenyl, 1-[2-[4-[1-(4-methoxyphenyl)-2-nitro-2-phenylethenyl]phenoxy]ethyl]-pyrrolidine which is available as the citrate salt from Parke-Davis Div. of Warner-Lambert Col, Morris Plains, N.J. under the name of Nitromifene Citrate, substituted aminoalkoxyphenylalkenes such as (Z)-2-[4-(1,2-diphenyl-1-butenyl)phenoxy]-N,N-dimethylethanamine which is available as the citrate salt from Stuart Pharmaceuticals, Wilmington, Del. as Tamoxifen Citrate (see also Belgian Patent No. 637,389, March 1964), 3,4-dihydro-2-(p-methoxyphenyl)-1-naphthyl p-[2-(1-pyrrolidinyl)ethoxy]phenyl ketone which is available as the methane sulfonate salt from Eli Lilly & Co. under the tradename of Trioxifene Mesylate, 1-[4'-(2-dimethylaminoethoxy)-phenyl)-1-(3'-hydroxyphenyl)-2-phenyl-but-1-ene, which is available from Klinge Pharma, 6-hydroxy-2-(p-hydroxyphenyl)-benzo(b)thien-3-yl[2-(1-pyrrolidinyl)-ethoxyphenyl]ketone which is available from Eli Lilly & Co. (LY-117018), [6-hydroxy-2-(4-hydroxyphenyl)benzo(b)thien-3-yl]-[4-(2-(1-piperdinyl)-ethoxy)phenyl]methanone, which is available from Eli Lilly & Co. as the hydrogen chloride salt (LY-156758) and meso-3,4-bis(3'-hydroxyphenyl)hexane as well as the dimethyl, dipropyl and 3'-acetoxyphenyl analogues which are described in U.S. Pat. No. 4,094,994 and a series of 1-phenyl-alkane and -alkenes, e.g. (E)-3-cyclopentyl-1-(4-hydroxyphenyl)-1-phenyl-1-butene and 2-cyclopentyl-1-[4-hydroxy-or methoxyphenyl]-3-phenyl-2-propen-1-ol and FC-1157 which is available as the citrate salt from Farmos Group, Ltd., Turku, Finland (see also Eur. Pat. Appln. EP 78,158). FC-1157, LY-117018, LY-156578 and Tamoxifen are the preferred antiestrogens.

In another preferred aspect of the present invention, an inhibitor of steroid biosynthesis such as 3-(4-aminophenyl)-3-ethyl-2,6-piperidinedione which is commonly called aminoglutethimide and is available from Ciba Pharmaceutical Col, Summit N.J. under tradename Cytadren or ketoconazole which is available from Janssen Pharmaceutica, Piscataway, N.J. under the tradename Nizoral is administered in combination with the LH-RH agonist or antagonist, the antiestrogen and the antiandrogen for treatment of breast cancer.

In this invention, the LH-RH agonist or antagonist, antiandrogen and antiestrogen are administered as pharmaceutical compositions via topical, parenteral or oral means. Preferably, the LH-RH agonist or antagonist is administered parenterally, i.e., intramuscularly, subcutaneously or intravenously by injection or infusion by nasal drops or intra-vaginally by suppository. The LH-RH agonist or antagonist also may be microencapsulated in or attached to a biocompatible, biodegradable polymer, e.g., poly(d,l-lactide-co-glycolide) and subcutaneously or intramuscularly injected by a technique called subcutaneous or intramuscular depot to provide continuous, slow release of the LH-RH agonist or antagonist over a period of 30 days or longer. The most preferred route of administration of the LH-RH agonist or antagonist is subcutaneous injection. Preferably the antiandrogen and antiestrogen will each be administered orally. Preferably the aminoglutethimide or ketoconazole are administered orally. The amount of each component administered is determined by the attending clinicians taking into consideration the etiology and severity of the disease, the patient's condition and age, the potency of each component and other factors. The LH-RH agonist or antagonist is generally administered at from about 10 to 2000 $\mu$g per day, with contemplated dosage ranges of 10 to 500 $\mu$g per day, 50–250 $\mu$g per day and 250 to 500 $\mu$g per day being preferred. In the most preferred embodiment of this invention, the LH-RH agonist or antagonist is administered subcutaneously in a daily dose of 500 $\mu$g for the first 30 days and thereafter subcutaneously in a daily dose of 250 $\mu$g regardless of the patients' body weight. When the LH-RH agonist or antagonist is administered, once every 30-day period, by intramuscular or subcutaneous depot injection, a dose from about 300 to 15000 $\mu$g per 30-day period is used, with a dose of 750 to 6000 $\mu$g per 30-day period being preferred. The antiandrogen compositions are generally administered in a dosage range of about 0.20 to 20 mg/kg (body weight) per day with 375 mg per day in three equally divided doses being preferred. The antiestrogen compositions are administered in a dosage range of about 0.1 to 10 mg/kg body weight per day, with 15 mg in three equally divided doses being preferred. The aminoglutethimide compositions when used are administered initially in a dosage of 250 mg given at 6-hour intervals and the dosage may be increased in increments of 250 mg daily up to a total daily dose of 2 grams. The ketoconazole compositions when used are administered orally in a dose of 200 mg once per day and may be increased to 800 mg once per day.

The LH-RH agonist or antagonist and anti-androgen and antiestrogen each may be administered separately or when the modes of administration are the same, all or two of them may be administered in the same composition, but in any case the preferred ratio of LH-RH agonist to antiandrogen to antiestrogen administered daily will be about 250 $\mu$g of LH-RH agonist to about 375 mg of antiandrogen to about 15 mg of antiestrogen.

In the most preferred aspect of this invention, the LH-RH agonist is [D-Trp$^6$, des-Gly NH$_2^{10}$]LH-RH ethylamide which is administered subcutaneously in single daily dose of 500 $\mu$g for the first thirty (30) days of treatment and thereafter in a single daily dose of 250 $\mu$g; the antiandrogen is 4'-nitro-3'-trifluoromethyl-isobutyranilide, i.e., flutamide, which is administered orally in three equally divided daily doses of 125 mg; and the antiestrogen is (Z)-2-[p-(1,2-diphenyl-1-butenyl)phenoxy]-N,N-dimethyl ethylamine (Tamoxifen) which is administered orally in three equally divided doses of 5 mg every 8 hours.

The antiestrogen and antiandrogen is preferably administered to a female in need of the breast cancer treatment of this invention one or two days before the LH-RH agonist or antagonist is administered, but the attending clinician may elect to start administration of the LH-RH agonist or antagonist, the antiandrogen and the antiestrogen on the first day of the treatment.

When patients whose ovaries have already been removed are treated according to this invention, the antiandrogen and the antiestrogen administration and dosage are the same as indicated when the antiandrogen and antiestrogen are used in combination with the LH-RH agonist or antagonist as well as the fourth ingredient, i.e. the inhibitor of steriod biosynthesis such as amino-glutethimide or ketoconazole.

The LH-RH agonist useful in the present invention are typically amorphous solids which are freely soluble in water or dilute acids, e.g., HCl, H$_2$SO$_4$, citric, acetic, mandelic or fumaric. The LH-RH agonist for subcutaneous injection is supplied in vials containing 6 mL of sterile solution with the LH-RH agonist at a concentration of about 1.0 mg/mL.

A typical pharmaceutical composition of the LH-RH agonists include the LH-RH agonist or a pharmaceutically acceptable acid salt thereof, benzyl alcohol, a phosphate buffer (pH=6.9–7.2) and sterile water.

The LH-RH agonist or antagonist for intramuscular or subcutaneous depot injection is microencapsulated in a biocompatible, biodegradable polymer, e.g., poly (d,l-lactide-co-glycolide) by a phase separation process. The microspheres are then suspended in a carrier to provide an injectable preparation.

The aminoglutethimide and ketoconazole are typically compounded in customary ways for oral administration, e.g., in tablets, capsules and the like.

The antiandrogens useful in the present invention are typically formulated with conventional pharmaceutical excipients, e.g., spray dried lactose and magnesium stearate into tablets or capsules for oral administration. The antiestrogens useful in the invention are typically compounded in customary ways for oral administration, e.g., in capsules, tablets, as dragees or even in liquid form, e.g., suspensions or syrups. One or more of the active substances, with or without additional types of active agents, can be worked into tablets or dragee cores by being mixed with solid, pulverulent carrier substances, such as sodium citrate, calcium carbonate or dicalcium phosphate, and binders such as polyvinyl pyrrolidone, gelatin or cellulose derivatives, possibly by adding also lubricants such as magnesium stearate, sodium lauryl sulfate, "Carbowax" or polyethylene glycols. Of course, taste-improving sub-stances can be added in the case of oral-administration forms.

The therapeutically active antiestrogen compound should be present in a concentration of about 0.5–90% by weight of the total mixture, i.e., in amounts that are sufficient for maintaining the above-mentioned range of dosage.

As further forms of administration, one can use plug capsules, e.g., of hard gelatin, as well as closed soft-gelatin capsules comprising a softner or plasticizer, e.g., glycerine. The plug capsules contain the active substance preferably in the form of granulate, e.g., in mixture with fillers, such as lactose, saccharose, mannitol, starches, such as potato starch or amylopectin, cellulose derivatives or highly-dispersed silicic acids. In soft-gelatin capsules, the active substance is preferably dissolved or suspended in suitable liquids, such as vegetable oils or liquid polyethylene glycols.

In place of oral administration, the active compounds may be administered parenterally. In such case, one can use a solution of the active substance, e.g., in sesame oil or olive oil.

Following the above treatment using the described regimen, breast tumor growth is inhibited and in some instances complete remission occurs.

What is claimed:

1. A method of treating breast cancer in a warm-blooded animal in need of such treatment which comprises blocking the ovarian hormonal secretions of said animal by surgical or chemical means and administering to said animal therapeutically effective amounts of an antiandrogen and an antiestrogen, or pharmaceutical compositions thereof.

2. The method of claim 1 wherein the ovaries are surgically removed.

3. The method of claim 1 wherein the ovarian hormonal secretions are blocked by administering an amount of a LH-RH agonist or a LH-RH antagonist or a pharmaceutical composition thereof effective to block said hormonal secretions.

4. The method according to claim 1 wherein the LH-RH agonist is administered parenterally together with a pharmaceutically acceptable parenteral carrier.

5. The method of claim 1 wherein the antiandrogen and the antiestrogen are each administered orally, together with a pharmaceutically acceptable oral carrier.

6. The method of claim 1 wherein the LH-RH agonist is a nonapeptide or a decapeptide represented by the formula: L-pyroglutamyl-L-histidyl-L-tryptophyl-L-seryl-L-tyrosyl-X-Y-L-arginyl-L-prolyl-Z, wherein X is D-tryptophyl, D-leucyl, D-alanyl, 3-(2-naphthyl)-D-alanyl, O-tert-butyl-D-seryl, D-tyrosyl, D-lysyl, D-phenylalanyl or N-methyl-D-alanyl and wherein Y is L-leucyl or D-leucyl or D-alanyl and wherein Z is glycyl-NHR$_1$ or NHR$_1$ wherein R$_1$ is H, lower alkyl or lower haloalkyl.

7. The method of claim 1 wherein the antiestrogen is (Z)-2-[4-(1,2-diphenyl-1-butenyl)phenoxy]-N,N-dimethylethanamine.

8. The method of claim 1 which further comprises administering aminoglutethimide or ketoconasole or pharmaceutical compositions thereof.

9. The method of claim 1 wherein the antiandrogen is 1-(3'-trifluoromethyl-4'-nitrophenyl)-4,4-dimethylimidazoline-2,5-dione.

10. The method of claim 1 wherein the antiandrogen is 4'-nitro-3'-trifluoromethylisobutyranilide.

11. A method of treating breast cancer in a warm-blooded animal having breast cancer whose ovarian hormonal secretions have been previously blocked by surgical or chemical means, which comprises administering to said animal therapeutically effective amounts of an antiandrogen and an antiestrogen, or pharmaceutical compositions thereof.

12. The method of claim 11 wherein the ovaries are surgically removed.

13. The method of claim 11 wherein the ovarian hormonal secretions are blocked by administering an amount of a LH-RH agonist or a LH-RH antagonist or a pharmaceutical composition thereof effective to block said hormonal secretions.

14. The method according to claim 11 wherein the LH-RH agonist is administered parenterally together with a pharmaceutically acceptable parenteral carrier.

15. The method of claim 11 wherein the antiandrogen and the antiestrogen are each administered orally, together with a pharmaceutically acceptable oral carrier.

16. The method of claim 11 wherein the LH-RH agonist is a nonapeptide or a decapeptide represented by the formula: L-pyroglutamyl-L-histidyl-L-tryptophyl-L-seryl-L-tyrosyl-X-Y-L-arginyl-L-prolyl-Z, wherein X is D-tryptophyl, D-leucyl, D-alanyl, 3-(2-naphthyl)-D-alanyl, O-tert-butyl-D-seryl, D-tyrosyl, D-lysyl, D-phenylalanyl or N-methyl-D-alanyl and wherein Y is L-leucyl or D-leucyl or D-alanyl and wherein Z is glycyl-NHR$_1$ or NHR$_1$ wherein R$_1$ is H, lower alkyl or lower haloalkyl.

17. The method of claim 11 wherein the anti-estrogen is (Z)-2-[4-(1,2-diphenyl-1-butenyl)phenoxy]-N,N-dimethylethanamine.

18. The method of claim 11 which further comprises administering aminoglutethimide or ketoconazole or pharmaceutical compositions thereof.

19. The method of claim 11 wherein the antiandrogen is 1-(3'-trifluoromethyl-4'-nitrophenyl)-4,4-dimethylimidazoline-2,5-dione.

20. The method of claim 11 wherein the antiandrogen is 4'-nitro-3'-trifluoromethylisobutyranilide.

21. A method of treating breast cancer in a warm-blooded animal having breast cancer which comprises administering to said animal therapeutically effective amounts of a LH-RH agonist or a LH-RH antagonist, an antiandrogen and an antiestrogen, or pharmaceutical compositions thereof.

22. The method of claim 21 wherein the LH-RH agonist is administered parenterally together with a pharmaceutically acceptable parenteral carrier.

23. The method of claim 18 wherein the antiestrogen and the antiandrogen are each administered orally, together with pharmaceutically acceptable oral carrier.

24. The method of claim 14 wherein the LH-RH agonist is administered at a daily parenteral dose of between 250 and 500 μg.

25. The method of claim 15 wherein the antiandrogen is administered at a daily oral dose of between about 0.20 and 20 mg and the antiestrogen is administered at a daily oral dose of between about 0.10 and 10 mg.

26. A kit comprising in separate containers pharmaceutical compositions for combined use in treating breast cancer which comprises (1) a pharmaceutical composition comprising an antiandrogen and (2) a pharmaceutical composition comprising an antiestrogen.

27. A kit comprising in separate containers pharmaceutical compositions for combined use in treating breast cancer which comprises (1) a pharmaceutical composition comprising a LH-RH agonist or a LH-RH antagonist (2) a pharmaceutical composition comprising an antiandrogen and (3) a pharmaceutical composition comprising an antiestrogen.

28. The kit of claim 27 wherein the pharmaceutical compositions are oral compositions.

29. The kit of claim 28 wherein the LH-RH agonist pharmaceutical composition comprises the LH-RH agonist in one container and a solvent for parenteral administration in another container.

30. The kit of claim 28 wherein the pharmaceutical compositions of the antiandrogen and the antiestrogen are each oral compositions 31. The method of inhibiting the growth of breast tumors in a warm blood animal whose ovarian hormonal secretions have been previously blocked by surgical or chemical means which comprises administering to the warm-blooded animal having such tumors therapeutically effective amounts of an antiandrogen and an antiestrogen, or pharmaceutical compositions thereof.

32. The method of claim 31 wherein the ovaries are surgically removed.

33. The method of claim 31 wherein the ovarian hrmonal secretions are blocked by administering and amount of a LH-RH agonist or a LH-RH antagonist or a pharmaceutical composition there of effective to block said hormonal secretions.

34. The method according to claim 31 wherein the LH-RH agonist is administered parenterally together with a pharmaceutically acceptable parenteral carrier 35. The method of claim 31 wherein the antiandrogen and the antiestrogen are each administered orally together with a pharmaceutically acceptable oral carrier.

36. The method of claim 31 wherein the LH-RH agonist is a nonapeptide or a decapeptide represented by the formula: L-pyroglutamyl-L-histidyl-L-tryptophyl-L-seryl-L-tyrosyl-X-Y-L-arginyl-L-prolyl-Z,
wherein X is D-tryptophyl, D-leucyl, D-alanyl, 3-(2-naphthyl)-D-alanyl, 0-tert-butyl-D-seryl, D-tyrosyl, D-lysyl, D-phenylalanyl or N-methyl-D-alanyl and wherein Y is L-leucyl or D-leucyl or D-alanyl and wherein Z is glycyl-NHR$_1$ or NHR$_1$ wherein R$_1$ is H, lower alkyl or lower haloalkyl.

37. The method of claim 31 wherein the antiestrogen is (Z)-2-[4-(1,2-diphenyl-1-butenyl)phenoxy]-N,N-dimethylethanamine.

38. The method of claim 31 which further comprises administering aminoglutethimide or ketoconasole or pharmaceutical compositions thereof.

39. The method of claim 31 wherein the antiandrogen is 1-(3'-trifluoromethyl-4'-nitrophenyl)-4,4-dimethylimidazoline-2,5-dione.

40. The method of claim 31 wherein the antiandrogen is 4'-nitro-3'-trifluoromethylisobutyranilide.

* * * * *